United States Patent
Koh

(10) Patent No.: US 7,636,600 B1
(45) Date of Patent: Dec. 22, 2009

(54) PRESSURE MONITORING FOR APNEA PREVENTION AND/OR THERAPY

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 423 days.

(21) Appl. No.: 11/255,379

(22) Filed: Oct. 21, 2005

(51) Int. Cl.
*A61N 1/37* (2006.01)

(52) U.S. Cl. ........................................ 607/42
(58) Field of Classification Search ........... 607/1, 607/2, 23, 42
See application file for complete search history.

(56) References Cited

U.S. PATENT DOCUMENTS

| | | | |
|---|---|---|---|
| 4,712,555 A | 12/1987 | Thornander et al. | 128/419 PG |
| 4,830,008 A | 5/1989 | Meer | 128/421 |
| 4,940,052 A | 7/1990 | Mann et al. | 128/419 PG |
| 4,944,298 A | 7/1990 | Sholder | 128/419 PG |
| 5,146,918 A * | 9/1992 | Kallok et al. | 607/2 |
| 5,466,254 A | 11/1995 | Helland | 607/123 |
| 5,476,483 A | 12/1995 | Bornzin et al. | 607/17 |
| 5,540,731 A * | 7/1996 | Testerman | 607/42 |
| 6,314,323 B1 | 11/2001 | Ekwall | 607/23 |
| 6,865,419 B2 * | 3/2005 | Mulligan et al. | 607/23 |
| 7,155,278 B2 * | 12/2006 | King et al. | 607/2 |
| 7,194,313 B2 * | 3/2007 | Libbus | 607/42 |
| 2003/0055345 A1 | 3/2003 | Eigler et al. | 600/486 |
| 2003/0153953 A1 | 8/2003 | Park et al. | 607/17 |
| 2003/0153955 A1 | 8/2003 | Park et al. | 607/17 |
| 2003/0204213 A1 | 10/2003 | Jensen et al. | 607/17 |
| 2005/0043772 A1 * | 2/2005 | Stahmann et al. | 607/42 |

FOREIGN PATENT DOCUMENTS

| | | |
|---|---|---|
| EP | 1 462 146 A1 | 9/2004 |
| WO | WO 03/092493 A2 | 11/2003 |
| WO | WO 03/092493 A3 | 11/2003 |

OTHER PUBLICATIONS

Ruzena Tkacova, MD, PhD, et al., "Overnight Shift From Obstructive to Central Apneas in Patients with Heart Failure—Role of Pco2 and Circulatory Delay", *Circulation*, Jan. 2001; vol. 103, pp. 238-243.

Stephane Garrigue et al., "Sleep Apnea: A New Indication for Cardiac Pacing?", *Pace*, Feb. 2004; vol. 27, pp. 204-211.

Thomas Hofman, MD, et al., "Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function", *J Am Coll Cardiol*, Jul. 1995; vol. 26, No. 1, pp. 239-249.

(Continued)

*Primary Examiner*—George R Evanisko
*Assistant Examiner*—Amanda Patton

(57) ABSTRACT

An exemplary method includes determining an intramural pressure based on one or more in vivo pressure measurements, based on the intramural pressure, deciding whether apnea exists and, if apnea exists, calling for one or more types of stimulation selected from a group consisting of autonomic nerve stimulation, phrenic nerve stimulation, diaphragm stimulation and cardiac stimulation. Other exemplary methods, devices, systems, etc., are also disclosed.

5 Claims, 14 Drawing Sheets

OTHER PUBLICATIONS

Tetsuo Shioi, MD, PhD, et al., "Rapamycin Attenuates Load-Induced Cardiac Hypertrophy in Mice", *Circulation*, Apr. 2003; vol. 107, pp. 1664-1670.

John Rogers et al., *"Cardiovascular System Review"*, pp. 1-9 http://www.tc.umn.edu/~humbu001/resources/summary_layout_cv.pdf.

John D. Parker et al., "Acute and Chronic Effects of Airway Obstruction on Canine Left Ventricular Performance", *Am J Respir Crit Care Med*, 1999; vol. 160, pp. 1888-1896.

Andrew Wellman, M.D., et al., "Atrial Pacing in Sleep Apnea Syndrome", *N Engl J Med*, Aug. 2002; vol. 347, No. 6, pp. 445-446.

* cited by examiner

Exemplary Sensor Locations 800

Pathways 900

Exemplary Method 1100

Exemplary Device 1300

Exemplary Methods 1400

Obstructive Apnea 1410

Central Apnea 1430

PRESSURE MONITORING FOR APNEA PREVENTION AND/OR THERAPY

FIELD OF THE INVENTION

Subject matter presented herein generally relates to determination of abnormal respiration such as apnea. Various exemplary methods, devices, systems, etc., concern use of an implantable device to aid in determination of abnormal respiration.

BACKGROUND

There is growing evidence that apnea plays a role in the progression of congestive heart failure (CHF) and that various forms of treatment can lead to improved outcomes. Obstructive sleep apnea (OSA) and central sleep apnea (CSA) occur quite commonly patients with CHF. In general, cardiac output decreases during apnea. For example, in OSA, repetitive pharyngeal collapses have been demonstrated to lower cardiac output by increasing the left ventricular transmural pressure, which is typically defined as the left ventricular pressure minus the intrathoracic pressure (see, e.g., Tkacova et al., "Overnight Shift From Obstructive to Central Apneas in Patients With Heart Failure: Role of PCO2 and Circulatory Delay", *Circulation* 2001; 103:238-243).

During airway collapse, intrathoracic pressure decreases substantially and thereby alters ventricular filling, which, in turn, worsens cardiac output. In some instances, such a mechanism may result in a shift from OSA episodes to CSA episodes (see, e.g., Garrigue et al. "Sleep Apnea: A New Indication for Cardiac Pacing?" *PACE* 27(2):204-211).

Adequate treatment of apnea and the detrimental effects of apnea rely on adequate detection. In particular, a detection technique should be able to distinguish OSA from CSA.

As described herein, various techniques rely on transmural pressure or information related to transmural pressure to detect apneic conditions. Various techniques further include calling for treatment of the conditions or the effects thereof.

SUMMARY

An exemplary method includes determining an intramural pressure based on one or more in vivo pressure measurements and, based on the intramural pressure, deciding whether apnea exists and, if apnea exists, calling for one or more types of stimulation selected from a group consisting of autonomic nerve stimulation, phrenic nerve stimulation, diaphragm stimulation and cardiac stimulation. Other exemplary methods, devices, systems, etc., are also disclosed.

In general, the various methods, devices, systems, etc., described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary methods, devices, systems, etc., described herein pertain to in vivo pressure measurements or surrogates thereof to aid in diagnosis of respiratory issues such as obstructive apnea and central apnea. Pressure measurement is optionally achieved using a suitably equipped implantable cardiac therapy device. Alternatively, an exemplary pressure measurement device or system is used to acquire pressure information. In turn, such an exemplary device or system may communicate with an implanted cardiac therapy device or an external device. An exemplary cardiac therapy device is described below that may receive information pertaining to respiration or may acquire pressure information pertaining to respiration. In various examples, flow or vessel size (e.g., one or more aorta dimensions) information may substitute for pressure information or be used in addition to pressure information.

Exemplary Stimulation Device

The techniques described below are optionally implemented in connection with any stimulation device that is configured or configurable to stimulate and/or shock tissue.

Figure 1:
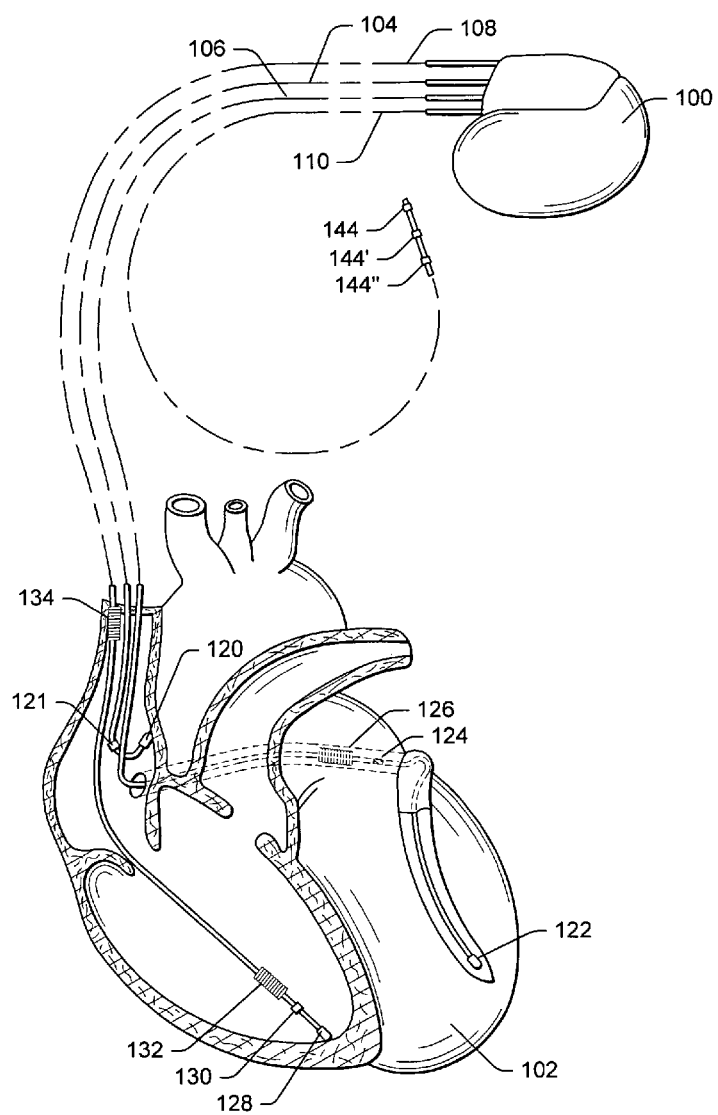
FIG. 1 is a simplified diagram illustrating an exemplary implantable stimulation device in electrical communication with at least three leads implanted into a patient's heart and at least one other lead for delivering stimulation and/or shock therapy. The exemplary stimulation device optionally includes one or more sensors for sensing pressure or information related to pressure.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
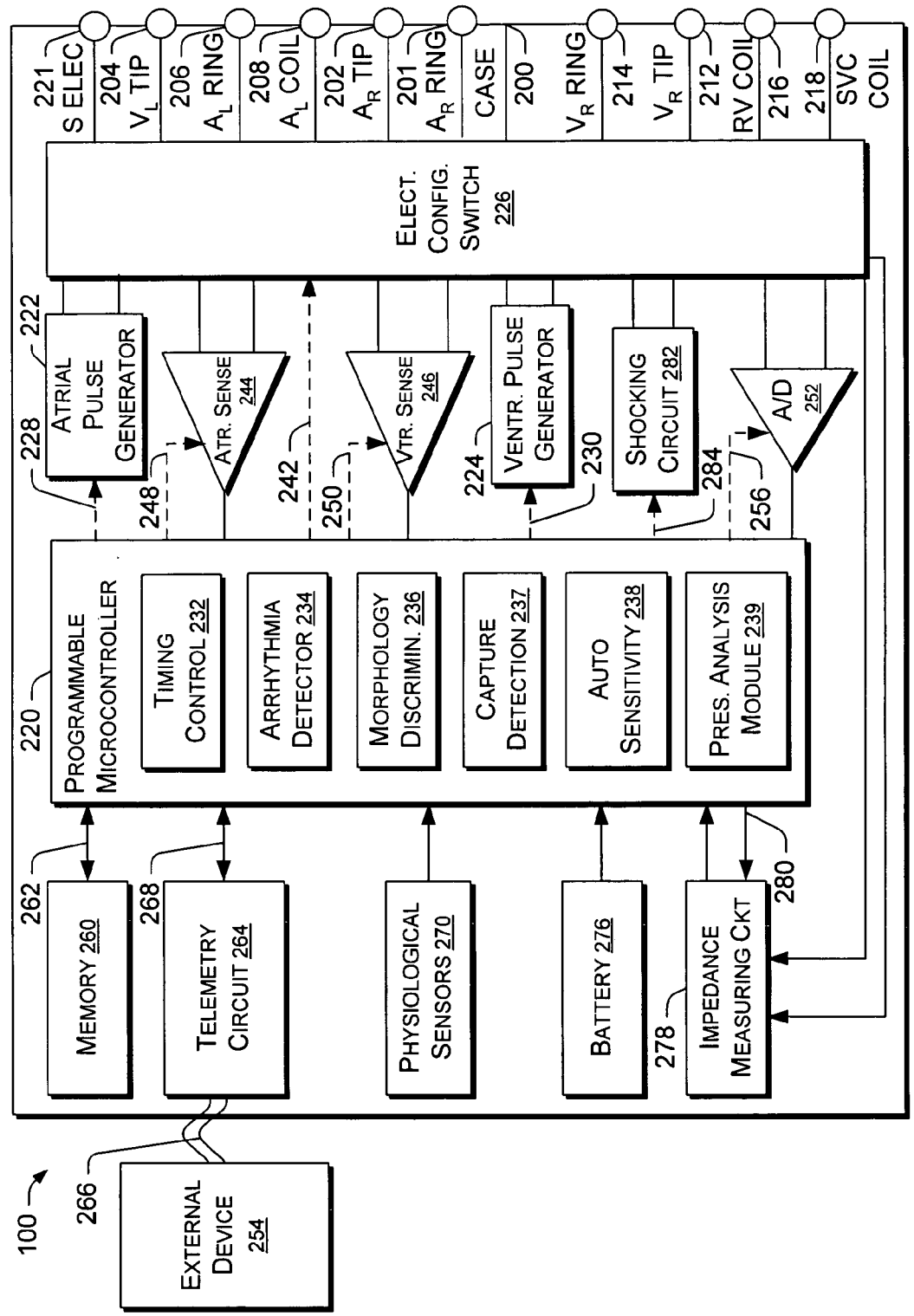
FIG. 2 is a functional block diagram of an exemplary implantable stimulation device illustrating basic elements that are configured to provide cardioversion, defibrillation, pacing stimulation or other tissue or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology discrimination module 236, a capture detection module 237, a auto sensitivity module 238, a pressure analysis module 239 and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The pressure analysis module 239 may perform a variety of tasks related to, for example, left atrial pressure, left ventricular pressure, aortic pressure, right atrial pressure, right ventricular pressure, etc. This component can be utilized by the stimulation device 100 in determining therapy in response to pressure, a derivative thereof, and/or other parameter. The pressure analysis module 239 may be implemented in hardware as part of the microcontroller 220, or as software/firmware instructions programmed into the device and executed on the microcontroller 220 during certain modes of operation. The pressure analysis module 239 may optionally implement various exemplary methods described herein. The pressure analysis module 239 may interact with the capture physiological sensors 270, the impedance measuring circuit 278 and optionally other modules. One or more of the physiological sensors 270 are optionally external to a pulse generator yet can provide information to the microcontroller 220.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

As already mentioned, the stimulation device 100 can further include or communicate with one or more physiologic sensors 270. The physiologic sensors 270 may be housed within the case 200, on the surface of the case 200 or external to the case 200. The one or more physiologic sensors optionally connect to the device 100 via one or more of the connectors or via other connectors. In some instances, a physiologic sensor may communicate with the microcontroller 220 via a wireless link. For example, a wristwatch physiologic sensor may communicate via electromagnetic radiation signals or other signals with a circuit in the device 100 (e.g., the telemetry circuit 264). Of course, an implantable physiologic sensor may also communicate with the device 100 via such communication means.

A physiologic sensor may be used to implement "rate-responsive" therapy where information sensed is used to adjust pacing stimulation rate according to, for example, the exercise state of the patient. A physiological sensor may be used to sense changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). The microcontroller 220 can respond to such information by adjusting any of the various pacing parameters (e.g., rate, AV Delay, V-V Delay, etc.) or anti-arrhythmia therapy parameters (e.g., timing, energy, leading edge voltage, etc.).

Pressure sensors for sensing left atrial pressure are discussed in U.S. Patent Application US 2003/0055345 A1, to Eigler et al., which is incorporated by reference herein. The discussion pertains to a pressure transducer permanently implantable within the left atrium of the patient's heart and operable to generate electrical signals indicative of fluid pressures within the patient's left atrium. According to Eigler et al., the pressure transducer is connected to a flexible electrical lead, which is connected in turn to electrical circuitry, which includes digital circuitry for processing electrical signals. Noted positions of the transducer include within the left atrium, within a pulmonary vein, within the left atrial appendage and in the septal wall.

The exemplary device 100 optionally includes a connector capable of connecting a lead that includes a pressure sensor. For example, the connector 221 optionally connects to a pressure sensor capable of receiving information pertaining to chamber pressures or other pressures. Pressure information is optionally processed or analyzed by the pressure analysis module 239.

A study by Hofmann et al., "Simultaneous measurement of pulmonary venous flow by intravascular catheter Doppler velocimetry and transesophageal Doppler echocardiography: relation to left atrial pressure and left atrial and left ventricular function", *J Am Coll Cardiol.* 1995 July; 26(1):239-49, used a "microtip" pressure transducer and noted that mean left atrial pressure was strongly correlated with the ratio of systolic to diastolic peak velocity, systolic velocity-time integral, time to maximal flow velocity and the ratio of systolic to diastolic flow duration. In particular, Hofmann et al. reported that the ratio of systolic to diastolic peak velocity and the time to maximal flow velocity were identified as strong independent predictors of mean left atrial pressure and that left atrial compliance was not found to be an independent predictor of mean left atrial pressure. This study indicates that surrogates may exist for indirect measurement or estimation of left atrial pressure or mean left atrial pressure.

Commercially available pressure transducers include those marketed by Millar Instruments (Houston, Tex.) under the mark MIKROTIP®. A study by Shioi et al., "Rapamycin Attenuates Load-Induced Cardiac Hypertrophy in Mice", *Circulation* 2003; 107:1664, measured left ventricular pressures in mice using a Millar pressure transducer inserted through the LV apex and secured in the LV apex with a purse-string suture using 5-0 silk. Various exemplary methods, devices, systems, etc., described herein optionally use such a pressure transducer to measure pressures in the body (e.g., chamber of heart, vessel, etc.).

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense pressure, respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device 100 optionally includes circuitry capable of sensing heart sounds and/or vibration associated with events that produce heart sounds. Such circuitry may include an accelerometer as conventionally used for patient position and/or activity determinations. Accelerometers typically include two or three sensors aligned along orthogonal axes. For example, a commercially available micro-electromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

While an accelerometer may be included in the case of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264. Trigger IEGM storage also can be achieved by magnet.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Figure 3:
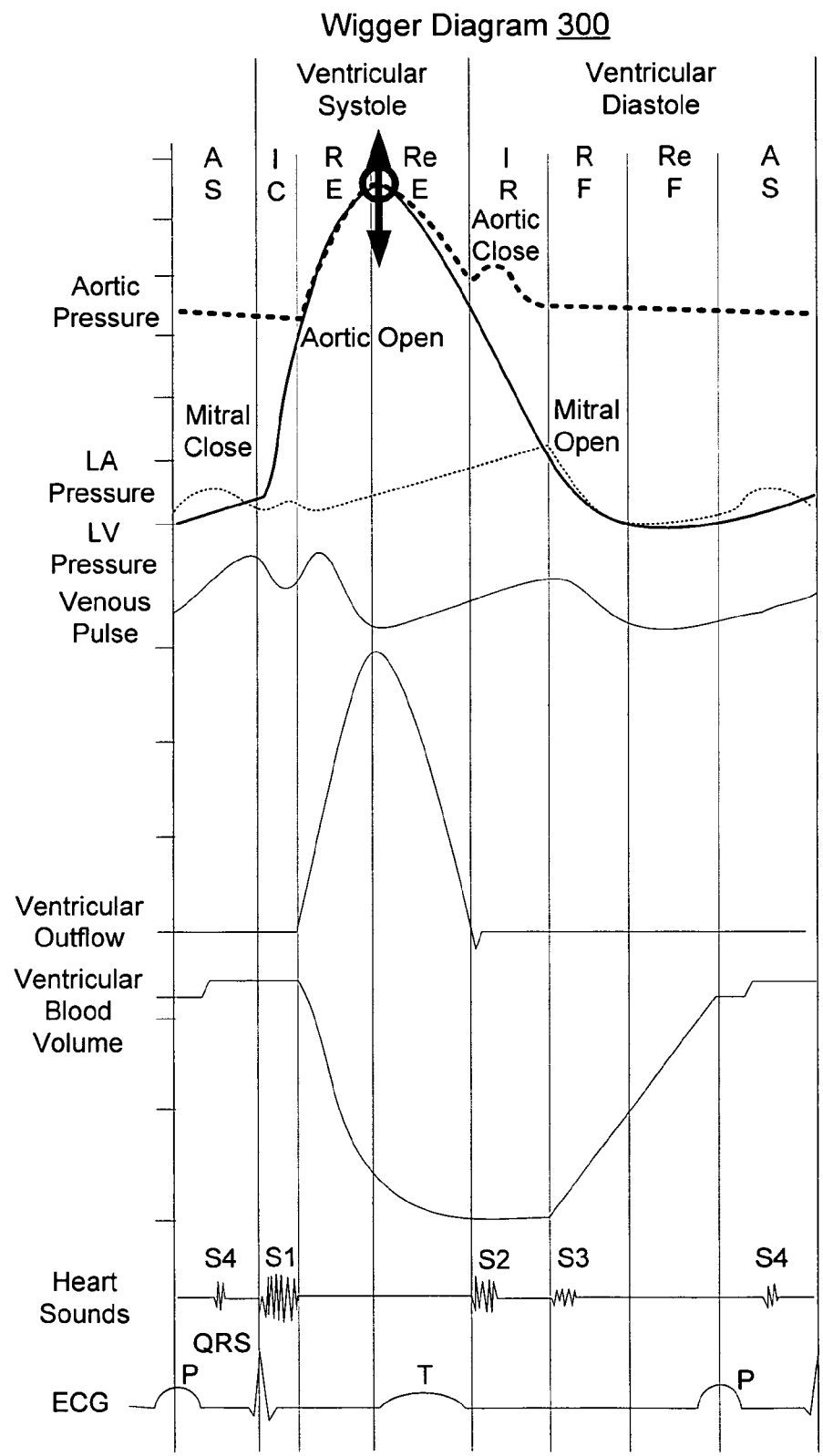
FIG. 3 is a diagram of various parameters and their variations during a cardiac cycle as typical of a Wigger diagram.

FIG. 3 shows a plot 300 of various parameters versus time during a cardiac cycle. The plot 300 is adapted from a Wigger diagram in an article entitled "Cardiovascular System Review" by Rogers and Humburg. The plot 300 shows various phases of the cardiac cycle including atrial systole (AS), isovolumic contraction (IS), rapid ejection (RE), reduced ejection (ReE), isovolumic relaxation (IR), rapid filling (RF), and reduced filling (ReF). In particular, the plot 300 illustrates how various parameters vary during ventricular systole and diastole. The parameters include aortic pressure, left atrial pressure, left ventricular pressure, venous pulse, ventricular outflow, ventricular volume, heart sounds, electrical activity (e.g., electrocardiogram) and valve dynamics. As described herein, any of a variety of parameters may be used to determine heart condition or respiration and to optionally adjust therapy.

The Wigger diagram 300 includes left ventricular pressure (P-LV) and aortic pressure (P-A). These pressure reach a maximum during the rapid ejection (RE) or reduced ejection (ReE) portions of ventricular systole. The maximum P-LV or P-A may be used to define the boundary between RE and ReE. The left ventricle supplies oxygenated blood to the aorta during systole, thus, the pressures follow similar paths during part of systole.

The Wigger diagram 300 includes a double headed arrow at the maximum P-LV and P-A. The arrow represents a relationship between respiration and the maximum pressure values. While relationships exist between various pressure values and respiration, the discussion below highlights the maximum P-LV and P-A. Where appropriate, mean or other values may be used.

Figure 4:
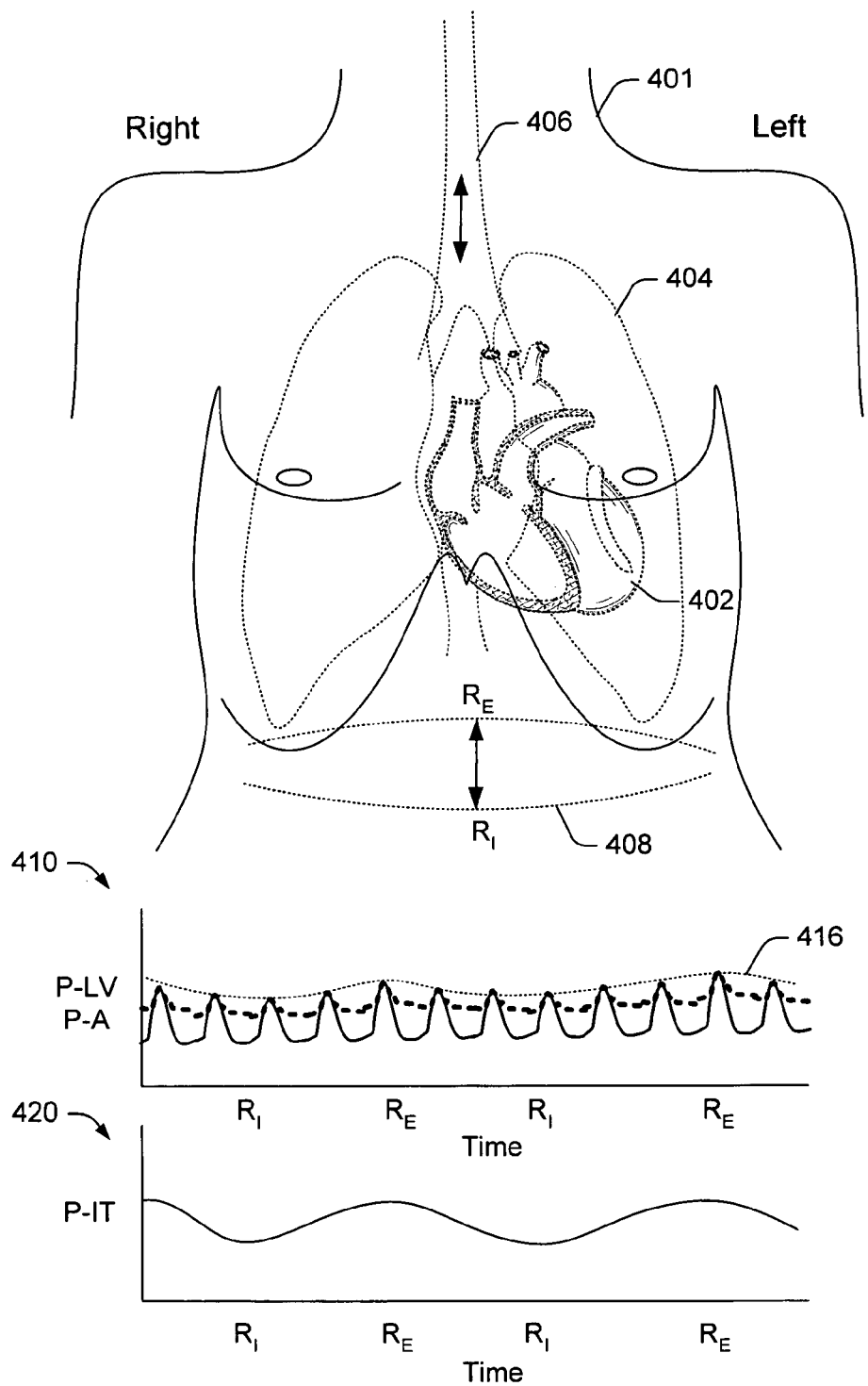
FIG. 4 is an exemplary schematic of normal respiration that includes plots of various pressure values versus time.

FIG. 4 shows a diagram of a human 401 including the heart 402, the lungs 404, the airway (trachea) 406 and the diaphragm 408 to illustrate normal respiration. FIG. 4 further includes a plot 410 of P-LV and P-A versus time and a plot 420 of intrathoracic pressure (P-IT) versus time. While intrathoracic pressure is shown in the plot 420, surrogates may exist. For example, a bronchial pressure, a tracheal pressure or other airway pressure may be used.

During respiration, the diaphragm 408 contracts as represented by the position labeled $R_I$, for inhalation or inspiration. During exhalation or expiration the diaphragm 408 relaxes as represented by the position $R_E$. As a consequence of the diaphragm's cycle, the intrathoracic pressure (P-IT) varies in a manner which causes air movement in the airway 406 to fill or to empty the lungs 404.

While mechanisms of respiration are complex, studies have shown that the change in P-IT due to respiration causes a corresponding change in P-LV and P-A. In general, P-LV and P-A decrease during inspiration (i.e., contraction of the diaphragm) and increase during expiration (i.e., relaxation of the diaphragm). The reasons for the change in P-LV and P-A may be attributed in major part to the decrease in P-IT, which decreases by about 5 mm Hg during inspiration (i.e., a pressure of −5 mm Hg). The plot 410 shows the variation of P-LV and P-A due to respiration, as represented by the dashed line 416. The pressures are not to scale but rather to illustrate changes due to respiration. Further, in this example, the respiration rate is slower than the heart rate, thus, more than one maximum P-LV or P-A measurement may be achieved during a respiratory cycle. In various examples, measurement of P-LV or P-A may be triggered by a declining P-IT measurement.

Figure 5:
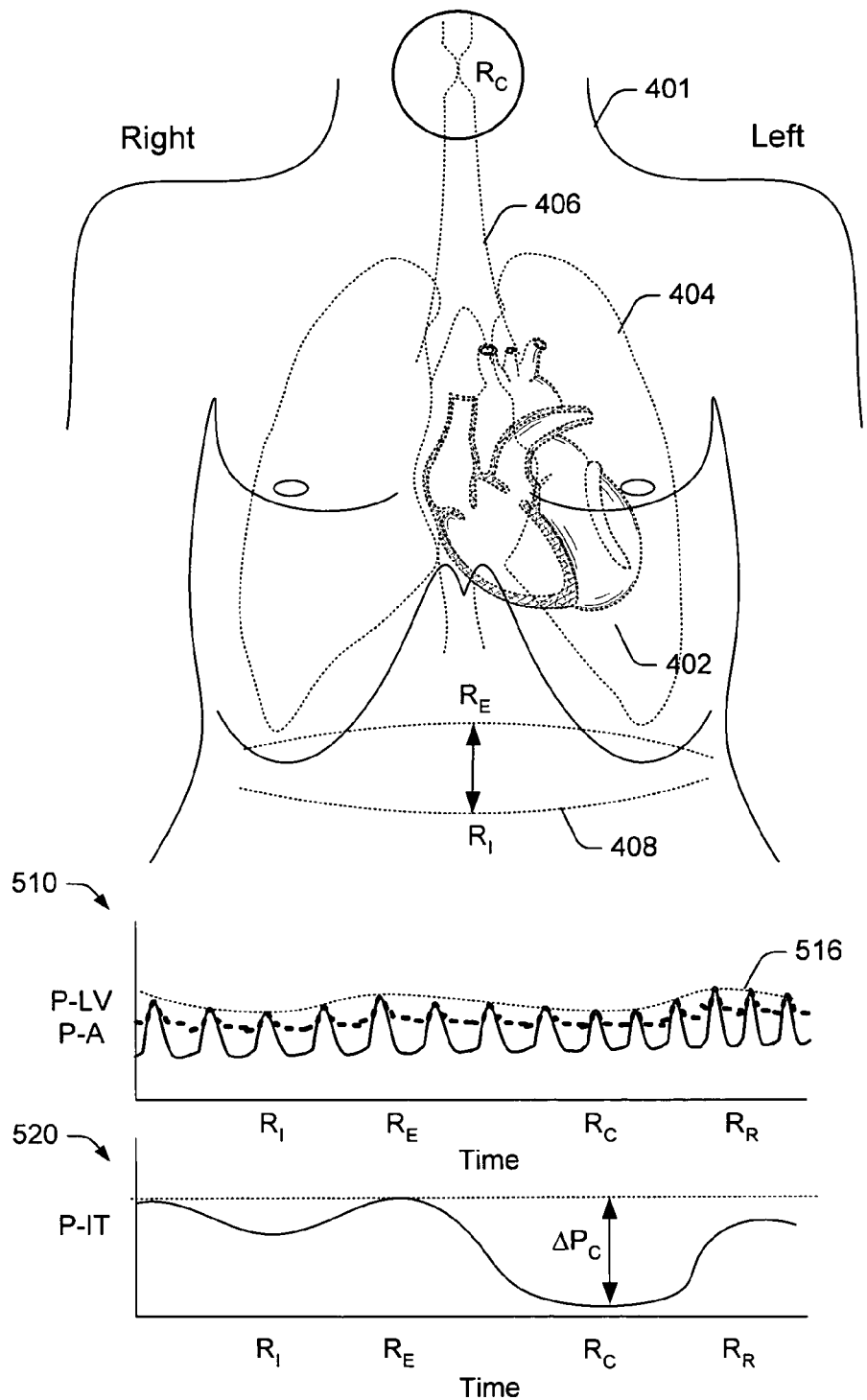
FIG. 5 is an exemplary schematic of abnormal respiration such as obstructive apnea that includes plots of various pressure values versus time.

FIG. 5 also shows a diagram of a human 401 including the heart 402, the lungs 404, the airway (trachea) 406 and the diaphragm 408 to illustrate obstructive apnea. FIG. 5 further includes a restricted region of the airway ($R_C$), a plot 510 of P-LV and P-A versus time and a plot 520 of intrathoracic pressure (P-IT) versus time. Again, while intrathoracic pressure is shown in the plot 520, surrogates may exist. For example, a bronchial pressure, a tracheal pressure or other airway pressure may be used.

Airway collapse ($R_C$) is associated with obstructive apnea and normally occurs during inspiration ($R_I$) when the upper airway muscles do not have patency sufficient to resist the negative intrathoracic pressure (e.g., ~−5 mmHg), which in turn causes expansion of the lungs and drawing in of air (i.e., from a higher pressure (e.g., atmospheric pressure) to a lower pressure). When collapse occurs, the diaphragm 408 does not immediately stop contracting and, in general, may contract more forcefully with accompanying onset of wakefulness from sleep, noting that in sleep apnea, onset of arousal typically demands more metabolic $O_2$. Together, the collapse and the diaphragm contraction (other respiratory muscles may be involved as well) cause P-IT to reach quite negative values well in excess of the about −5 mmHg associated with normal respiration. For example, a study by Parker et al., entitled "Acute and Chronic Effects of Airway Obstruction on Canine Left Ventricular Performance", *Am J Respir Crit Care Med* 1999; 160:1888-1896, reported negative airway pressures (tracheal pressures) in excess of −60 mmHg in canines. Parker et al. also reported a significant corresponding drop in P-LV, although much less than −60 mmHg.

The plot 520 of P-IT versus time illustrates a pressure drop associated with airway collapse ($\Delta P_C$), which is several times larger than the pressure drop associated with normal respiration. The plot 510 indicates that an observable corresponding change may occur in P-LV and P-A (see, e.g., dashed line 516); however, the decrease in P-LV and P-A do not equal the decrease in P-IT.

Figure 6:
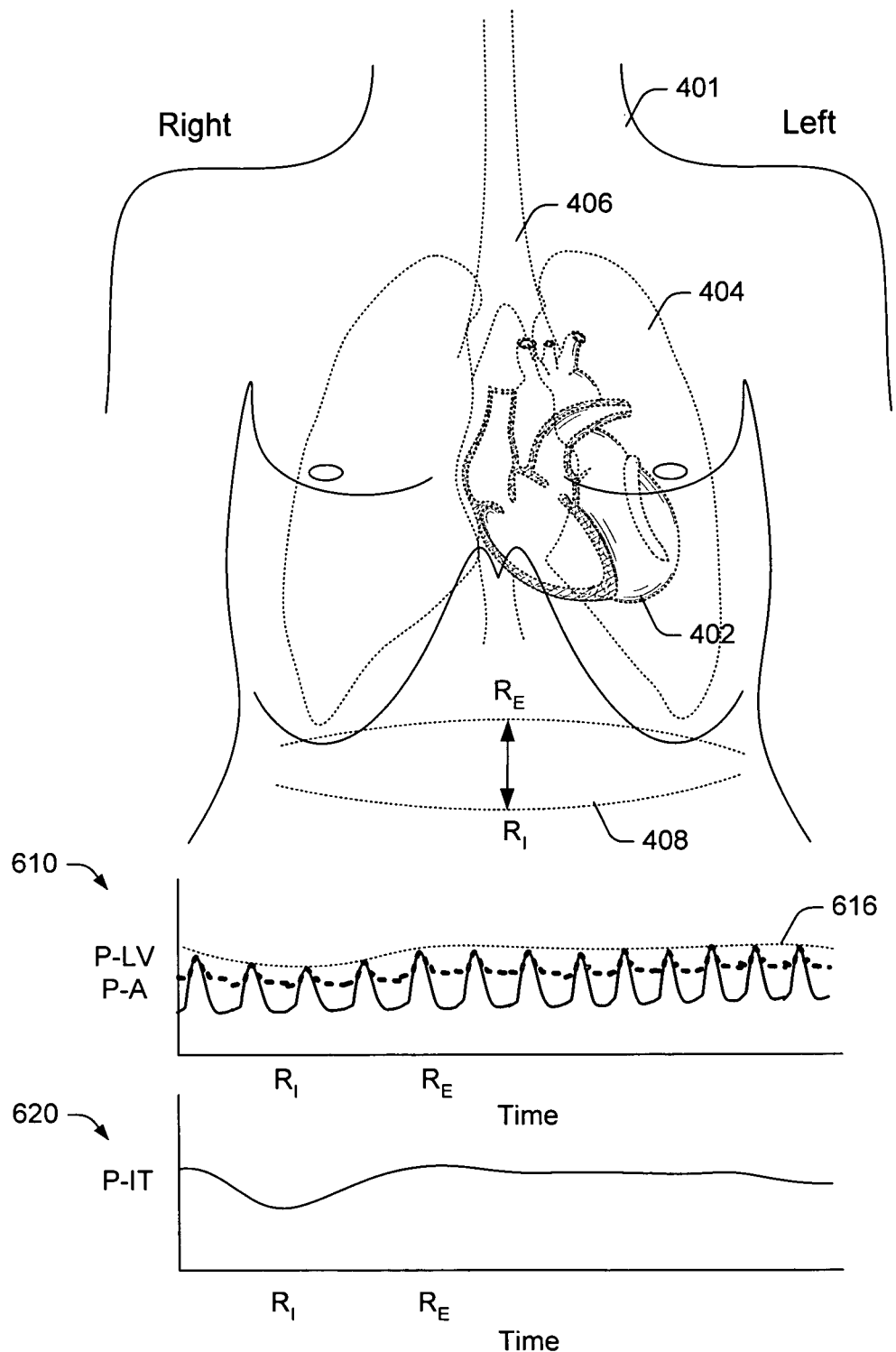
FIG. 6 is an exemplary schematic of abnormal respiration such as central apnea that includes plots of various pressure values versus time.

FIG. 6 also shows a diagram of a human 401 including the heart 402, the lungs 404, the airway (trachea) 406 and the diaphragm 408 to illustrate central apnea. FIG. 6 further includes a plot 610 of P-LV and P-A versus time and a plot 620 of intrathoracic pressure (P-IT) versus time. Again, while intrathoracic pressure is shown in the plot 620, surrogates may exist. For example, a bronchial pressure, a tracheal pressure or other airway pressure may be used.

In central apnea, the diaphragm does not contract in manner sufficient to cause a negative intrathoracic pressure (P-IT) and consequently, respiration is abnormal. The plot 620 indicates that P-IT is essentially constant for some period of time. In turn, the plot 610 indicates that maximum P-LV and P-A do not vary as respiration has essentially ceased (see, e.g., dashed line 616).

The study by Parker et al. relied on tracheal pressure measurements and left ventricular measurements via a catheter inserted via the right carotid artery. In particular, a 2-Fr micromanometer catheter (Model SPC-320); Millar Industries) was used for LV pressure measurements. Parker et al. calculated transmural LV pressure during airway occlusions as the LV pressure minus the simultaneously measured tracheal pressure, which they assumed to reflect intrathoracic pressure.

Figure 7:
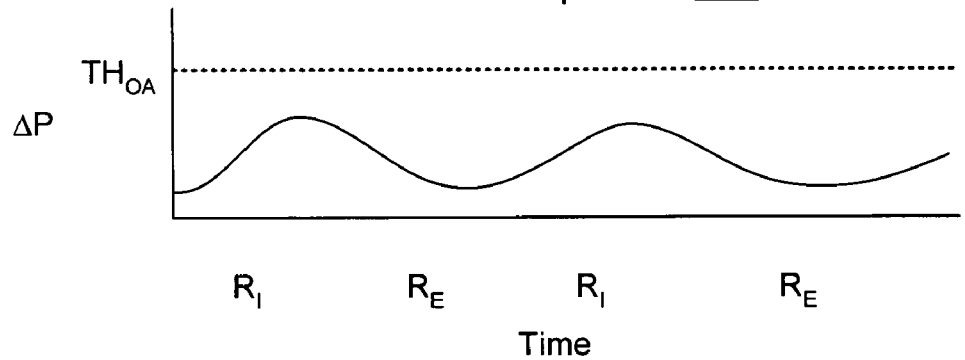
FIG. 7 is a series of exemplary plots of transmural pressure versus time for various respiratory conditions.
Figure 7:
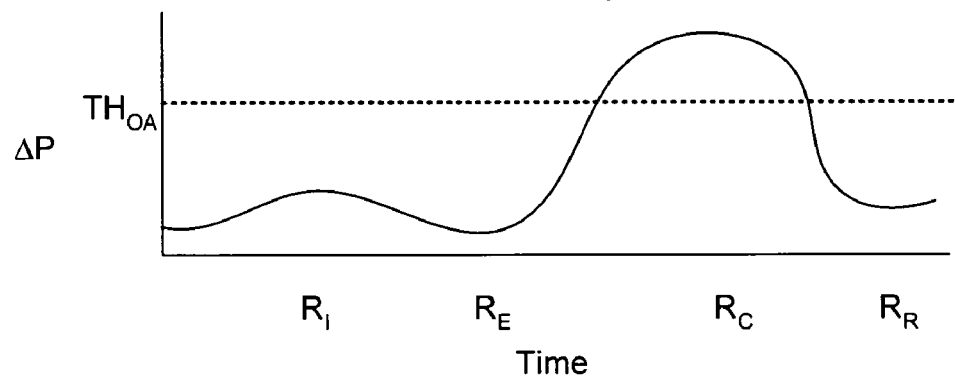
Figure 7:
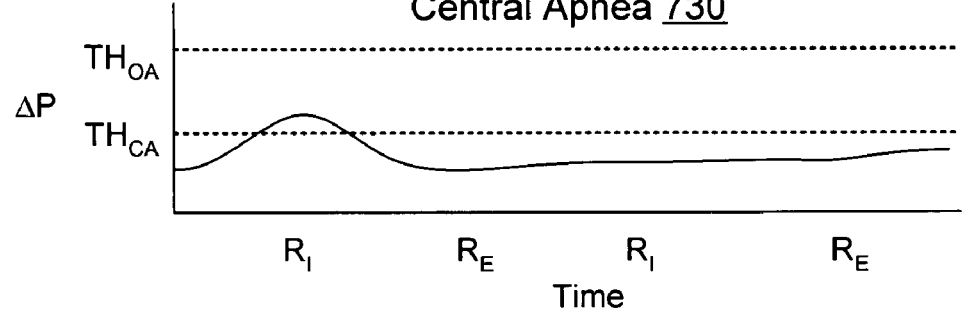

FIG. 7 shows a series of plots 710, 720, 730 of a transmural pressure versus time for various scenarios. The plot 710 corresponds to normal respiration where the transmural pressure ($\Delta P$) is less than a threshold value ($TH_{OA}$) indicative of an obstructive apnea. The plot 720 corresponds to an obstructive apnea where the transmural pressure ($\Delta P$) is exceeds a threshold pressure value ($TH_{OA}$) indicative of an obstructive apnea. The plot 730 corresponds to a central apnea where the transmural pressure ($\Delta P$) is essentially constant for an extended period of time as indicated by a central apnea threshold pressure ($TH_{CA}$) that is not exceeded. The period of time that the ($\Delta P$) fails to exceed the threshold may be decided in any of a variety of manners. For example, a period equivalent to three average sleep respiratory cycles may be used.

Various exemplary methods, devices, systems, etc., described herein optionally rely on comparison of a transmural pressure to one or more thresholds to determine if respiration is abnormal. In particular, an exemplary method may rely on such a comparison to distinguish obstructive apnea from central apnea. In turn, an exemplary method may call for therapy to minimize occurrence of future apnea, to improve cardiac output, to increase upper airway muscle tone for improved patency, etc.

Figure 8:
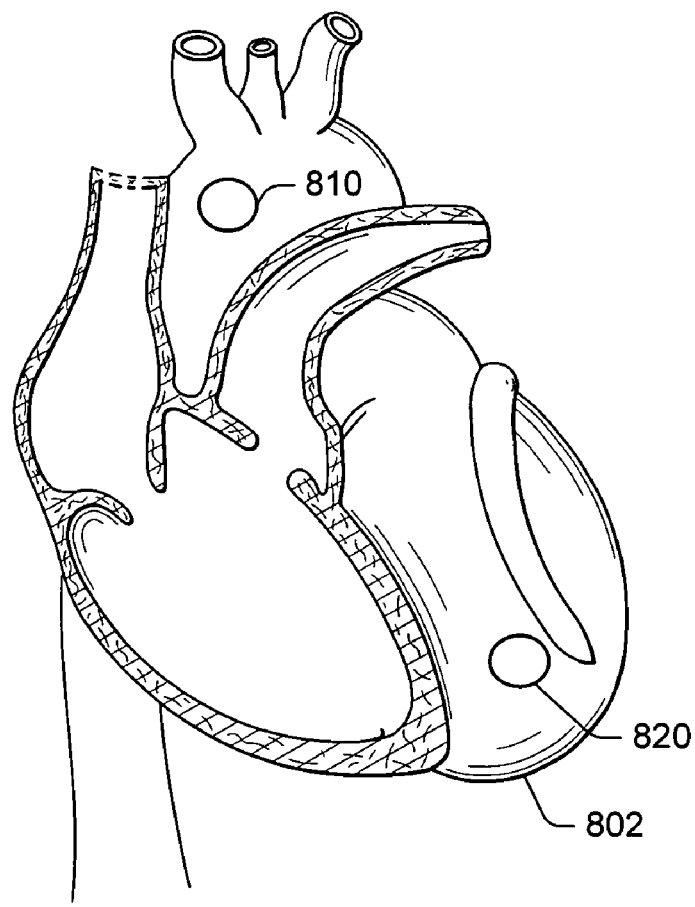
FIG. 8 is a diagram that includes exemplary sensor positions for sensing transmural pressure or information related thereto.

FIG. 8 shows exemplary sensor locations 800 with reference to a heart 802. One sensor location 810 is associated with the aorta. Such a sensor may measure aorta pressure, aorta flow, aorta size, etc. Such a sensor may be capable of measuring a pressure differential between an aortic pressure and an intrathoracic pressure. An exemplary sensor optionally measures a force where the force corresponds to the sum of an aortic force due to pumping action of the heart and an intrathoracic force due to action of the diaphragm or a lack thereof.

Another sensor location 820 is associated with the left ventricle. Such a sensor may measure left ventricular pressure, left ventricular size, etc. Such a sensor may be capable of measuring a pressure differential between a left ventricular pressure and an intrathoracic pressure. An exemplary sensor optionally measures a force where the force corresponds to the sum of a left ventricular force due to pumping action of the heart and an intrathoracic force due to action of the diaphragm or a lack thereof.

An exemplary sensor optionally includes two or more ports to allow for generation of one or more differential pressures. For example, a two port differential pressure transducer may include a membrane that separates a first chamber connected to a first port and a second chamber connected to a second port. The membrane may deflect or other respond to a difference between the chamber pressures in a manner that can generate an electrical signal for use by a processor of an exemplary implantable device (see, e.g., the device 100 of FIGS. 1 and 2 and the exemplary pressure module 239). An exemplary differential pressure sensor may be part of an exemplary implantable device or may be in communication with an exemplary implantable device such as the device 100. Ports of an exemplary pressure sensor may be in direct pressure communication with a particular region of the body (e.g., tissue, fluid or cavity) or may be in communication with a particular region or regions of the body via one or more conduits.

Figure 9:
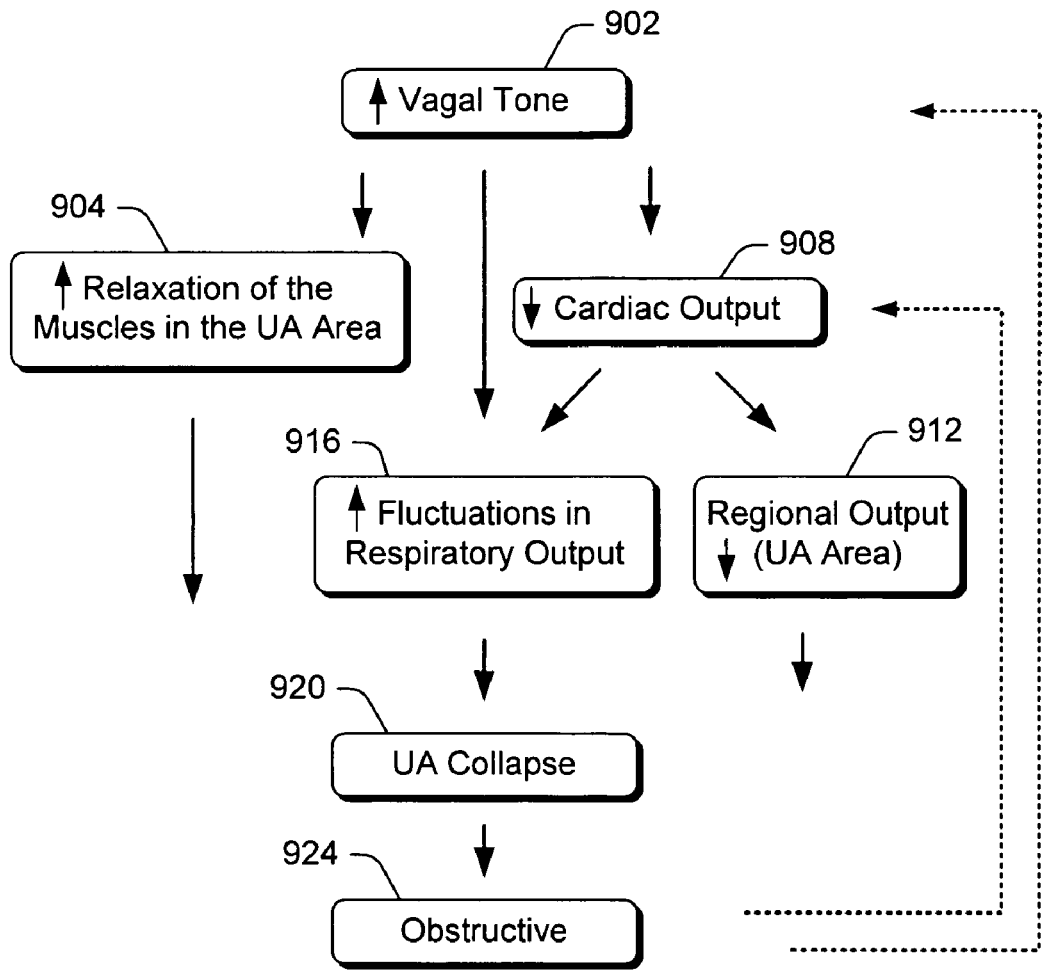
FIG. 9 is a schematic of pathways related to obstructive apnea, vagal tone and cardiac performance.

FIG. 9 shows various pathways or mechanisms 900 related to obstructive sleep apnea from nocturnal bradycardia induced by hypervagotonia with or without alteration of left ventricular performance. In some instances, hypervagotonia (elevated vagal tone 902) can induce relaxation of the upper airway muscles 904 that leads to a collapse of the upper airway 920 upon contraction of the diaphragm. Hypervagotonia 902 induced nocturnal bradycardia can induce, simultaneously, a lower cardiac output 908 that reduces blood flow to region of the upper airway muscles 912 and fluctuations in respiratory output 916. Occurrence of obstructive apnea 924 further acts to increase hypervagotonia 902.

As already described, obstructive apnea acts to increase the left ventricular transmural pressure. Consequences of such an elevation in transmural pressure include alteration of ventricular filling and reduction in cardiac output. The latter may cause a shift from obstructive apnea episodes to central apnea episodes. Thus, various exemplary methods, devices, systems, etc., may detect obstructive apnea and take appropriate action to prevent central apnea. Such action may include autonomic nerve stimulation, diaphragm activation (e.g., phrenic nerve stimulation), cardiac stimulation, etc.

Figure 10:
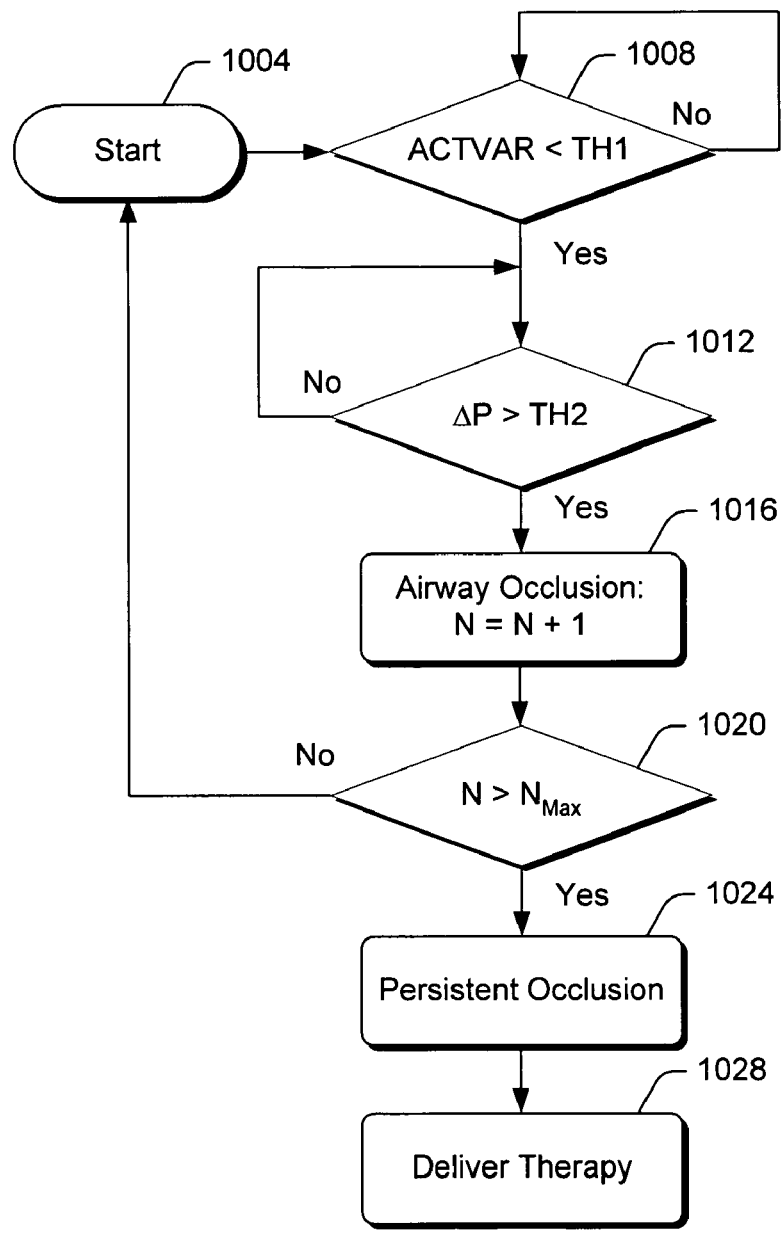
FIG. 10 is a block diagram of an exemplary method for deciding whether apnea exists and responding to apnea with appropriate therapy.

FIG. 10 shows an exemplary method 1000 for monitoring intramural pressure and optionally delivering therapy. The method 1000 commences in a start block 1004, which may initiate acquisition of intramural pressure information (e.g., $\Delta P$) or may initiate analysis of intramural pressure information. A decision block 1008 decides if the variation (ACT-VAR) in the intramural pressure (per the information) has exceeded some threshold (TH1). The variation may be standard deviation, another statistical value, etc. The threshold TH1 is generally of a lesser value than the obstructive apnea threshold $TH_{OA}$ discussed earlier and indicates that suspect variations are occurring in the intramural pressure ($\Delta P$). If the decision block 1008 decides that the variations in intramural pressure ($\Delta P$) do not exceed the threshold TH1, then monitoring continues. However, if the variations exceed the threshold TH1, then the method 1000 enters another decision block 1012.

The decision block 1012 decides if the intramural pressure ($\Delta P$) exceeds a threshold value TH2 (e.g., $TH_{OA}$). If the intramural pressure ($\Delta P$) does not exceed the threshold, monitoring continues. However, if the intramural pressure ($\Delta P$) exceeds the threshold TH2, then the method 1000 determines that an occlusion has occurred and it enters an index increment block 1016 (e.g., N=N+1). The index block 1016 acts to track the number of occurrences of occlusions, optionally with respect to time.

Yet another decision block 1020 decides if the index "N" has exceeded a maximum value "$N_{Max}$". If the decision block 1020 decides that the number of occlusions in a period of time has not exceeded a maximum, then the method 1000 continues at the start block 1004 where the method may reinitiate, optionally resetting the counter depending on the time of a prior occurrence. However, should the index exceed the maximum, then the method 1000 continues in a determination block 1024 that determines that the occlusions are persistent and perhaps of a certain character (e.g., frequency, pattern, etc.). In response, the method 1000 enters a delivery block 1028 to deliver an appropriate therapy.

The therapy called for by the delivery block 1028 may call for nerve stimulation, cardiac stimulation, diaphragm activation, etc. For example, where vagal tone is excessive, sympathetic nerve stimulation may act to adjust the autonomic balance. Cardiac stimulation may act to increase cardiac output. Diaphragm activation may act to cause inspiration where central apnea is an issue.

Figure 11:
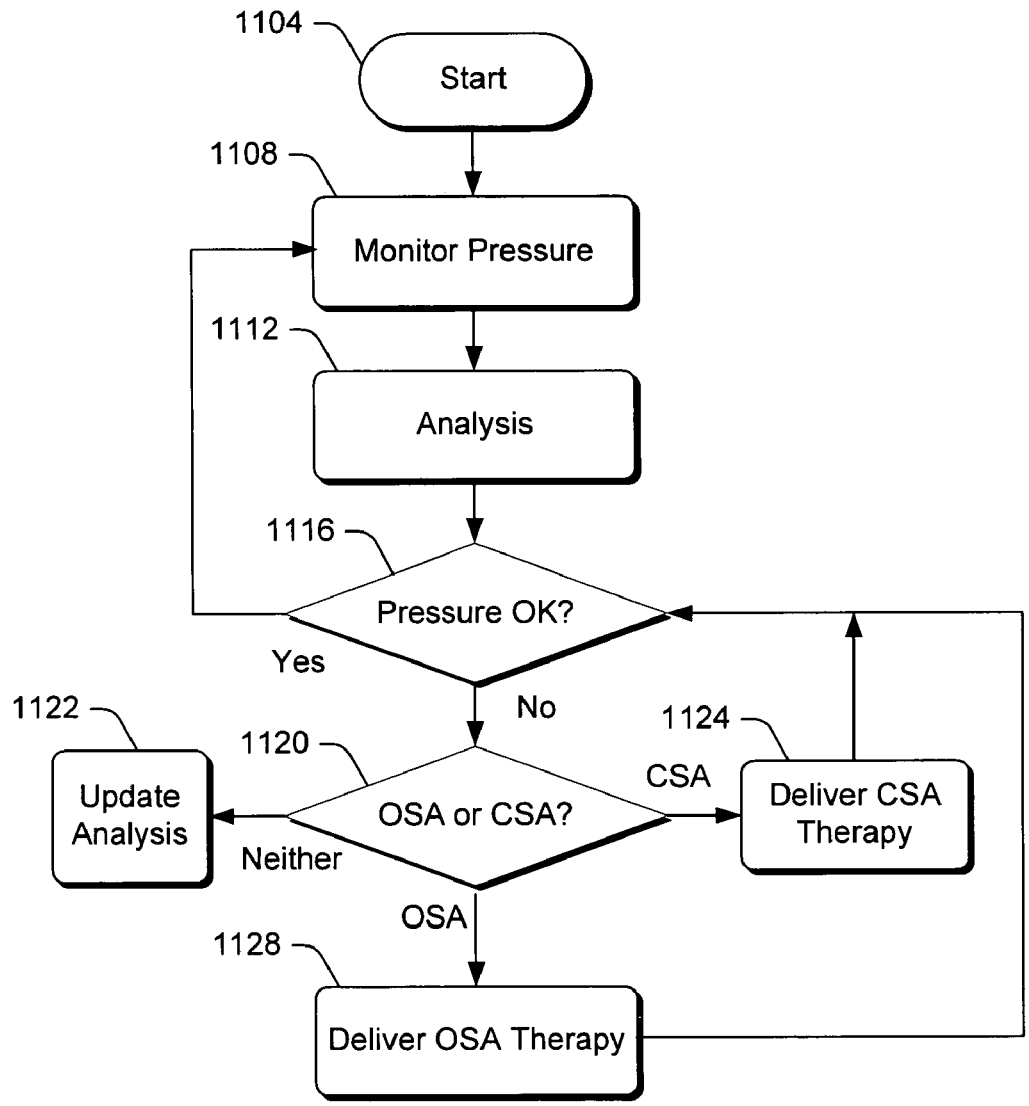
FIG. 11 is a block diagram of an exemplary method for delivering therapy for apnea.

FIG. 11 shows an exemplary method 1100 that monitors pressure and decides whether to deliver therapy based at least in part on pressure. The method 1100 commences in a start block 1104. The start block 1104 may act to implement the following steps at night or when a patient is otherwise at rest or at risk of experiencing apnea. A monitor block 1108 monitors a pressure differential such as an intramural pressure (P-IT). An analysis block 1112 analyzes the pressure information, for example, using statistical or other techniques. For example, referring to the plots 420, 520, 620 of P-IT versus time, normal respiration and abnormal respiration exhibit various features. The analysis block 1112 may determine a normal mean pressure and an associated standard deviation wherein if the pressure exceeds a limit based on the mean and the standard deviation, then obstructive apnea (OSA) may exist; whereas, if the pressure falls below a limit based on the mean and the standard deviation, then central apnea (CSA) may exist.

A decision block 1116 follows the analysis block 1112 wherein the results of the analysis are used to decide if the pressure is OK with respect to one or more criteria (e.g., the aforementioned limits, etc.). If the decision block 1116 decides that the pressure is OK, then the method 1100 continues at the monitor pressure block 1108 or other appropriate block. However, if the decision block 1116 decides that there the pressure does not meet the one or more criteria, then another decision block 1120 decides if obstructive sleep apnea (OSA) or central sleep apnea exists (CSA). The decision block 1120 may also decide that neither OSA or CSA are indicated and enter an analysis update block 1122 to update a pressure information analysis (e.g., per the analysis block 1112).

If the decision block 1120 decides that OSA exists, then the method 1100 enters a delivery block 1128 for delivery of OSA therapy whereas if the decision block 1120 decides that CSA exists, then the method 1100 enters a delivery block 1124 for delivery of CSA therapy. After delivery of an appropriate therapy, the method 1100 may continue at the decision block 1116 or at another block. Counters or timers may be used to direct the exemplary method 1100 to repeat an action, take other action or terminate.

Figure 12:
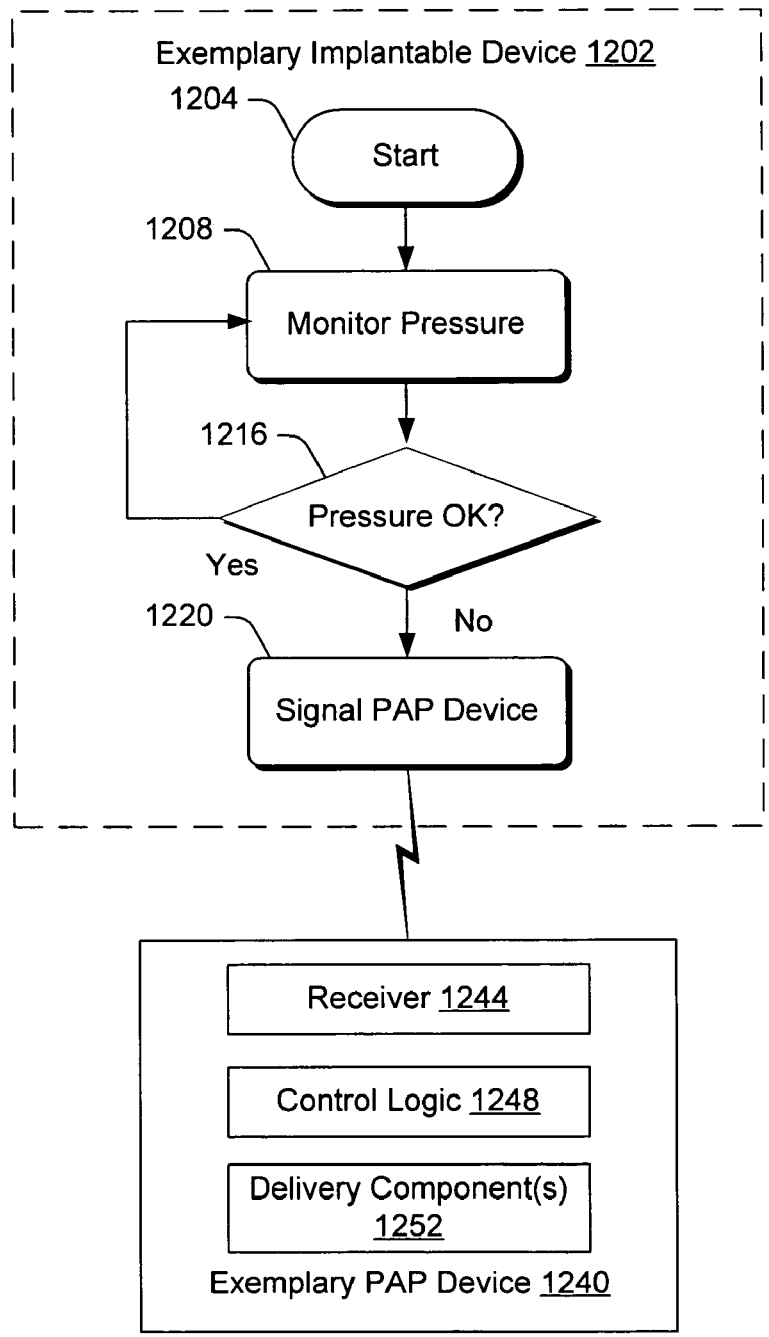
FIG. 12 is a block diagram of an exemplary method and system for signaling an exemplary positive airway pressure device based on information acquired by an exemplary implantable device.

FIG. 12 shows an exemplary method and system 1200 for delivering therapy via an exemplary positive airway pressure device (PAP) 1240. The exemplary system 1200 includes an exemplary implantable device 1202 and the exemplary PAP device 1240. The exemplary method 1200 operates predominantly within the exemplary implantable device 1202, which may include various features of the exemplary device 100 of FIGS. 1 and 2.

The exemplary method 1200 monitors pressure and decides whether to deliver therapy based at least in part on pressure. The method 1200 commences in a start block 1204. The start block 1204 may act to implement the following steps at night or when a patient is otherwise at rest or at risk of experiencing apnea. A monitor block 1208 monitors a pressure differential such as an intramural pressure (P-IT). A decision block 1216 follows that decides if the pressure is OK, for example, based on one or more pressure criteria. If the decision block 1216 decides that the pressure is OK, then the method 1200 continues in the monitor block 1208. However, if the decision block 1216 decides that the pressure is not OK (e.g., per one or more criteria), then the method 1200 continues in a signal block 1220 that communicates a signal to the exemplary PAP device 1240.

The exemplary PAP device 1240 includes a receiver 1244, control logic 1248 and one or more components to delivery therapy 1252 (e.g., positive airway pressure to a patient). The receiver 1244 is optionally relies on telemetry such as the circuit 264 of the exemplary device 100 of FIG. 2. Control logic 1248 uses the signal communicated from the implantable device 1202 to determine an appropriate therapy for delivery by the delivery component(s) 1252. For example, the signal may indicate an airway obstruction and, in turn, the control logic may cause the delivery component(s) 1252 to increase pressure or otherwise adjust a delivery parameter. The PAP device 1240 optionally communicates with the implantable device 1202; however, the implantable device 1202 may be able to sense operation of the PAP device 1240 via the pressure monitoring. In either instance, warnings or other information may be issued to improve or assure patient therapy, patient condition, device condition, etc.

Figure 13:
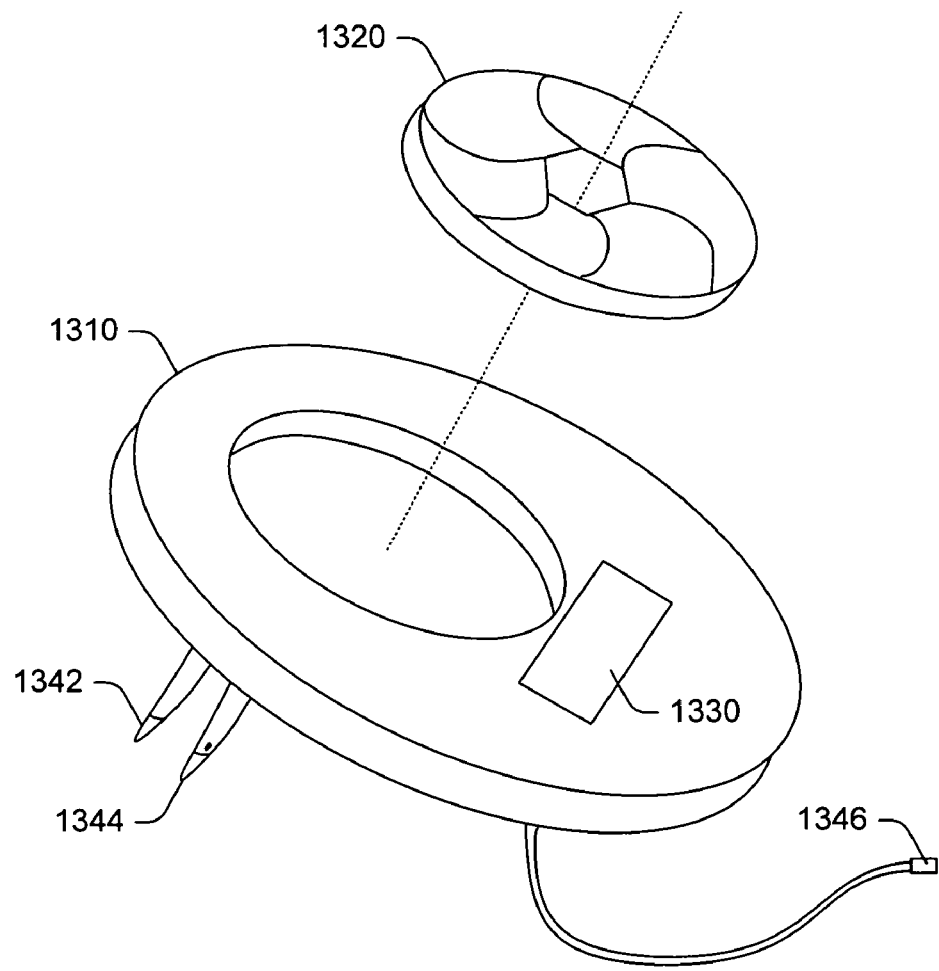
FIG. 13 is a diagram of an exemplary device that includes a shutter for opening a passage to the airway.

FIG. 13 shows an exemplary device 1300 that includes a shutter 1320 to allow for airflow to a patient's airway. The device 1300 includes a body 1310 that houses various components. For example, components 1342 and 1344 are sensors such as a temperature sensor and a pressure sensor that may be positioned to sense airway temperature and airway pressure, respectively. A lead 1346 includes one or more electrodes for delivery of stimuli, for example, to stimulate muscles or nerves (e.g., the phrenic nerve). A shutter control mechanism 1330 operates to control the shutter 1320 and optionally the shutter aperture's flow area. The control mechanism 1330 optionally includes a solenoid. In another example, a shutter includes louvers that may be opened or closed via a control mechanism. The shutter 1320 is optionally removable for service or cleaning. The shutter 1320 is optionally constructed of stainless steel.

The exemplary device 1300 can respond to sensed information to control the shutter 1320. The exemplary device 1300 optionally includes a timer that allows for timed operation of the shutter 1320. For example, the timer may be programmed to open the shutter 1320 during sleeping hours to ensure that a pathway for airflow exists in the case of airway obstruction (i.e., obstructive apnea).

The exemplary device 1300 may be implanted or surface positioned at any suitable location and preferably on the ventral side of a patient's body where the shutter 1320 is positioned where a tracheotomy opening would be positioned. The exemplary device 1300 optionally include communication circuitry to communicate in a wired or wireless manner with other devices, such as, a programmer or an implanted device (e.g., a pacemaker, etc.). Where communication with a pacemaker or other cardiac therapy device exists, the exemplary device 1300 may communicate sensed information or signal the cardiac therapy device when apnea occurs. In turn, the cardiac therapy device may implement an appropriate therapy.

Figure 14:
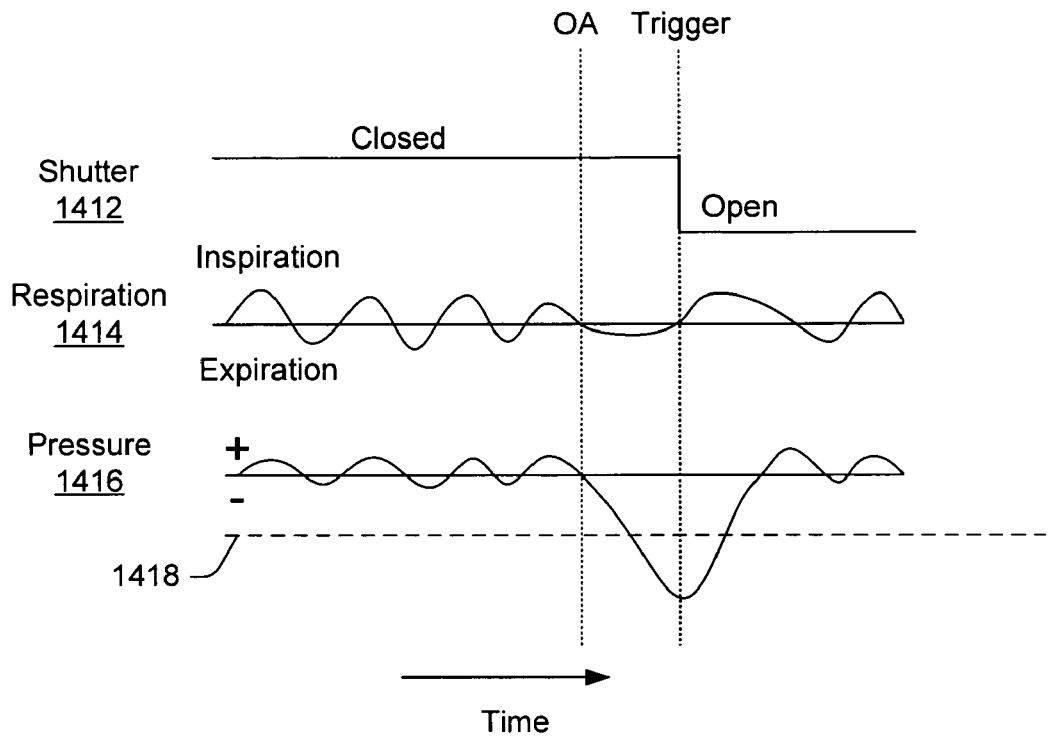
FIG. 14 is a diagram of a timeline for an exemplary method for treating obstructive apnea and a timeline for an exemplary method for detecting central apnea.
Figure 14:
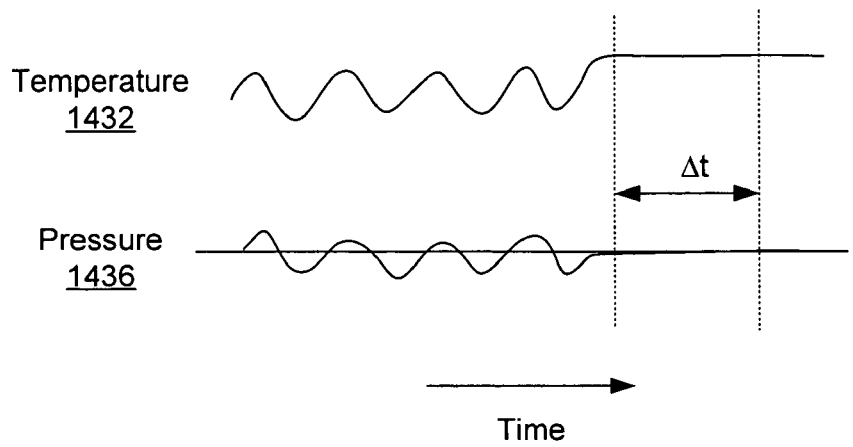

FIG. 14 shows exemplary methods 1400 for using information sensed by the exemplary device 1300 or other sensors positioned with respect to a patient's airway to sense temperature and pressure information or surrogates thereof. An exemplary method 1410 for treating obstructive apnea. The exemplary method 1410 is shown with respect to sensed information and control action. In particular, respiration information 1414 or pressure information 1416 is acquired and then used in deciding whether a shutter should be open or closed. Of course, finer control may decide degree of shutter opening, timing, etc.

At some point in time, obstructive apnea (OA) occurs. The OA causes the airway pressure to decrease below a limit 1418. When this occurs, pressure information is monitored to determine if the pressure continues to drop. As shown, the pressure continues to drop and consequently, the method 1410 calls for opening of the shutter 1412. Upon opening of the shutter 1412, respiration returns.

An exemplary method 1430 for detecting central apnea relies on temperature information 1432 and pressure information 1436 (e.g., as sensed by the sensors 1342, 1344 of the exemplary device 1300). If these values settle to substantially constant values for a period of time (Dt), then this indicates the presence of central apnea. Accordingly, appropriate action may be taken via stimulation (e.g., the lead 1346) or via patient alert.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
   measuring an in vivo left ventricular pressure and an intrathoracic pressure;
   determining an intramural pressure based on the in vivo differential pressure measurement of the left ventricular pressure and the intrathoracic pressure;
   based on the intramural pressure, deciding whether central sleep apnea or obstructive sleep apnea exists; and
   if obstructive apnea exists, calling for one or more of autonomic nerve stimulation, phrenic nerve stimulation, diaphragm stimulation, or cardiac stimulation.

2. The method of claim 1 wherein the deciding compares the intramural pressure to a threshold pressure value.

3. The method of claim 1 wherein the deciding compares the intramural pressure to one or more threshold pressure values.

4. A method comprising:
   measuring an in vivo aortic pressure and an intrathoracic pressure;
   determining an intramural pressure based on the in vivo differential pressure measurement of the aortic pressure and the intrathoracic pressure;
   based on the intramural pressure, deciding whether central sleep apnea or obstructive sleep apnea exists; and
   if obstructive apnea exists, calling for one or more of autonomic nerve stimulation, phrenic nerve stimulation, diaphragm stimulation, or cardiac stimulation.

5. An implantable device comprising:
   a processor;
   one or more sensors adapted to measure an in vivo left ventricular pressure and an intrathoracic pressure; and
   control logic adapted to determine an intramural pressure based on the in vivo differential pressure measurement of the left ventricular pressure and the intrathoracic pressure, adapted to decide whether central sleep apnea or obstructive sleep apnea exists based on the intramural pressure, and adapted to call for one or more of autonomic nerve stimulation, phrenic nerve stimulation, diaphragm stimulation or cardiac stimulation if obstructive sleep apnea exists.

* * * * *

UNITED STATES PATENT AND TRADEMARK OFFICE
CERTIFICATE OF CORRECTION

PATENT NO. : 7,636,600 B1
APPLICATION NO. : 11/255379
DATED : December 22, 2009
INVENTOR(S) : Steve Koh It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 834 days.

Signed and Sealed this

Ninth Day of November, 2010

David J. Kappos
*Director of the United States Patent and Trademark Office*